(12) United States Patent
Huang

(10) Patent No.: US 10,815,773 B2
(45) Date of Patent: Oct. 27, 2020

(54) FLOW MEASUREMENT INSERT

(71) Applicant: SCHLUMBERGER TECHNOLOGY CORPORATION, Sugar Land, TX (US)

(72) Inventor: Songming Huang, Cambridge (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 120 days.

(21) Appl. No.: 15/779,009

(22) PCT Filed: Nov. 22, 2016

(86) PCT No.: PCT/US2016/063213
§ 371 (c)(1),
(2) Date: May 24, 2018

(87) PCT Pub. No.: WO2017/091523
PCT Pub. Date: Jun. 1, 2017

(65) Prior Publication Data
US 2019/0032477 A1  Jan. 31, 2019

(30) Foreign Application Priority Data

Nov. 24, 2015 (GB) .................................. 1520706.1

(51) Int. Cl.
*E21B 47/10* (2012.01)
*G01F 1/74* (2006.01)
(Continued)

(52) U.S. Cl.
CPC ........... *E21B 47/101* (2013.01); *G01D 21/02* (2013.01); *G01F 1/42* (2013.01); *G01F 1/44* (2013.01);
(Continued)

(58) Field of Classification Search
CPC ..... E21B 47/101; E21B 47/107; G01D 21/02; G01N 33/2823; G01F 1/42; G01F 1/74; G01F 1/662
See application file for complete search history.

(56) References Cited

U.S. PATENT DOCUMENTS 3,951,159 A   4/1976   Robinson et al.
4,435,196 A   3/1984   Pielkenrood
(Continued)

FOREIGN PATENT DOCUMENTS

CN   2397476 Y    9/2000
CN   201788135 U  4/2011
(Continued)

OTHER PUBLICATIONS

Monkhouse, R. S. C. et al., "Flexible interdigital PVDF transducers for the generation of Lamb waves in structures", Ultrasonics, 1997, 35, pp. 489-498.
(Continued)

*Primary Examiner* — John Fitzgerald

(57) ABSTRACT

A multiphase flow measurement insert for insertion within a pipe includes a first, upstream isolation disc sized and shaped so as to make a fluid tight seal with the interior surface of the pipe. A second, downstream isolation disc is also sized and shaped to make a fluid tight seal with the interior surface of the pipe. The first isolation disc includes a first orifice and the second isolation disc includes a second orifice. The lower edge of the first orifice is positioned vertically higher in the first isolation disc than the lower edge of the second orifice in the second isolation disc. A measurement vessel extends from the first orifice to the second orifice forming a flow channel that is downwardly sloping when the multiphase flow measurement insert is in its operational orientation.

20 Claims, 10 Drawing Sheets

(51) Int. Cl.

| | | |
|---|---|---|
| *G01D 21/02* | (2006.01) | |
| *G01K 13/02* | (2006.01) | |
| *G01F 1/42* | (2006.01) | |
| *G01F 1/66* | (2006.01) | |
| *G01F 1/44* | (2006.01) | |
| *G01N 33/28* | (2006.01) | |

(52) U.S. Cl.
  CPC .............. *G01F 1/662* (2013.01); *G01F 1/74* (2013.01); *G01K 13/02* (2013.01); *G01N 33/2823* (2013.01)

(56) References Cited

U.S. PATENT DOCUMENTS

| | | | |
|---|---|---|---|
| 4,660,414 A | 4/1987 | Hatton et al. | |
| 5,127,272 A | 7/1992 | Dean et al. | |
| 5,396,807 A | 3/1995 | Dowty et al. | |
| 5,561,245 A | 10/1996 | Georgi et al. | |
| 5,576,495 A | 11/1996 | Vetterick | |
| 5,708,211 A | 1/1998 | Jepson et al. | |
| 6,575,043 B1 | 6/2003 | Huang et al. | |
| 6,758,100 B2 | 7/2004 | Huang | |
| 7,650,799 B2 | 1/2010 | Atkinson et al. | |
| 8,322,228 B2* | 12/2012 | Xie | G01F 1/36 73/861.04 |
| 8,555,729 B2* | 10/2013 | Xie | G01F 1/36 73/861.04 |
| 8,640,529 B2* | 2/2014 | Sinha | G01F 1/66 73/61.45 |
| 8,694,270 B2 | 4/2014 | Huang et al. | |
| 8,806,955 B2 | 8/2014 | McDole et al. | |
| 9,234,779 B2* | 1/2016 | Sinha | G01F 1/667 |
| 9,383,237 B2 | 7/2016 | Wiklund et al. | |
| 10,612,368 B2* | 4/2020 | Vincelette | G01N 29/2431 |
| 2007/0006640 A1 | 1/2007 | Gysling | |
| 2007/0204750 A1 | 9/2007 | Liu et al. | |
| 2008/0163692 A1 | 7/2008 | Huang et al. | |
| 2008/0319685 A1* | 12/2008 | Xie | G01N 22/00 702/45 |
| 2009/0090504 A1 | 4/2009 | Weightman et al. | |
| 2009/0139345 A1 | 6/2009 | Xie | |
| 2009/0229556 A1 | 9/2009 | Delgado | |
| 2010/0192703 A1 | 8/2010 | Huang et al. | |
| 2011/0048564 A1 | 3/2011 | Wible et al. | |
| 2011/0098938 A1 | 4/2011 | Huang et al. | |
| 2011/0112773 A1 | 5/2011 | Atkinson | |
| 2011/0259120 A1 | 10/2011 | Thonstad | |
| 2012/0055262 A1* | 3/2012 | Sinha | G01F 1/66 73/861.04 |
| 2012/0073540 A1 | 3/2012 | Gangl | |
| 2014/0060204 A1 | 3/2014 | Nakla et al. | |
| 2014/0109684 A1* | 4/2014 | Sinha | G01F 1/667 73/861.04 |
| 2015/0185062 A1* | 7/2015 | Ahmad | G01F 1/74 73/861.04 |
| 2018/0320505 A1* | 11/2018 | Vincelette | G01N 29/14 |
| 2018/0348035 A1* | 12/2018 | Huang | G01F 15/00 |
| 2018/0356314 A1* | 12/2018 | Lagus | G01N 1/2035 |

FOREIGN PATENT DOCUMENTS

| | | | |
|---|---|---|---|
| CN | 104075759 A | * | 10/2014 |
| EP | 0972171 A1 | | 1/2000 |
| GB | 1206294 A | | 9/1970 |
| NL | 2014629 A | * | 6/2015 |
| WO | 0111190 A1 | | 2/2001 |
| WO | 2007057708 A2 | | 5/2007 |
| WO | 2015153133 A1 | | 10/2015 |

OTHER PUBLICATIONS

First Office Action of Chinese Patent Application No. 21680068691.6, dated Oct. 11, 2019, 25 pages.
Combined Search and Examination Report under Sections 17 and 18(3) of UK Patent Application No. 1520708.7, dated May 23, 2016, 6 pages.
Examination Report under Section 18(3) of UK Patent Application No. 1520708.7, dated Oct. 18, 2018, 3 pages.
Office Action in U.S. Appl. No. 15/779,024, dated Nov. 4, 2019.
International Preliminary Report on Patentability of International Patent Application No. PCT/US2016/063212, dated Jun. 7, 2018, 11 pages.
Search Report and Written Opinion of International Patent Application No. PCT/US2016/063212, dated Mar. 10, 2017, 15 pages.
Combined Search and Examination Report under Sections 17 and 18(3) of UK Patent Application No. 1520706.1, dated May 14, 2016, 5 pages.
Examination Report under Section 18(3) of UK Patent Application No. 1520706.1, dated Oct. 18, 2018, 4 pages.
Search Report and Written Opinion of International Patent Application No. PCT/US2016/063213, dated Mar. 20, 2017, 12 pages.
International Preliminary Report on Patentability of International Patent Application No. PCT/US2016/063213, dated Jun. 7, 2018, 9 pages.
First Chinese Office Action in Chinese Patent Application No. 210680068724.7, dated Oct. 28, 2019, 11 pages.
Office Action in RU Patent Application No. 2018122458, dated Mar. 11, 2020, 14 pages.
Notice of Allowance in U.S. Appl. No. 15/779,024, dated Mar. 13, 2020, 12 pages.

* cited by examiner

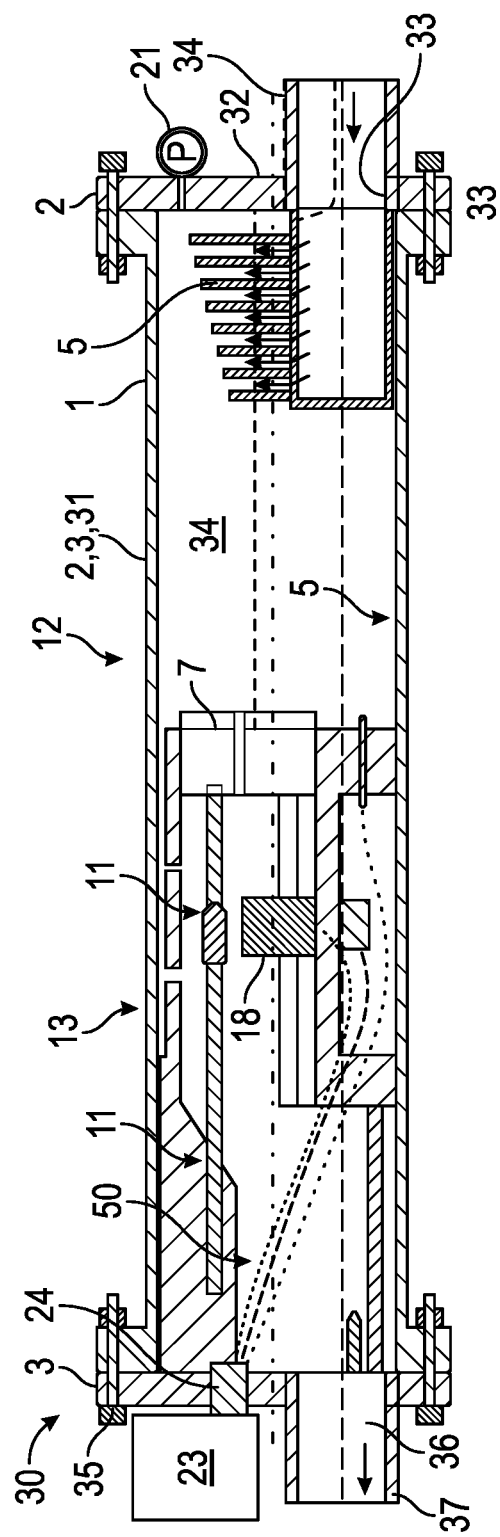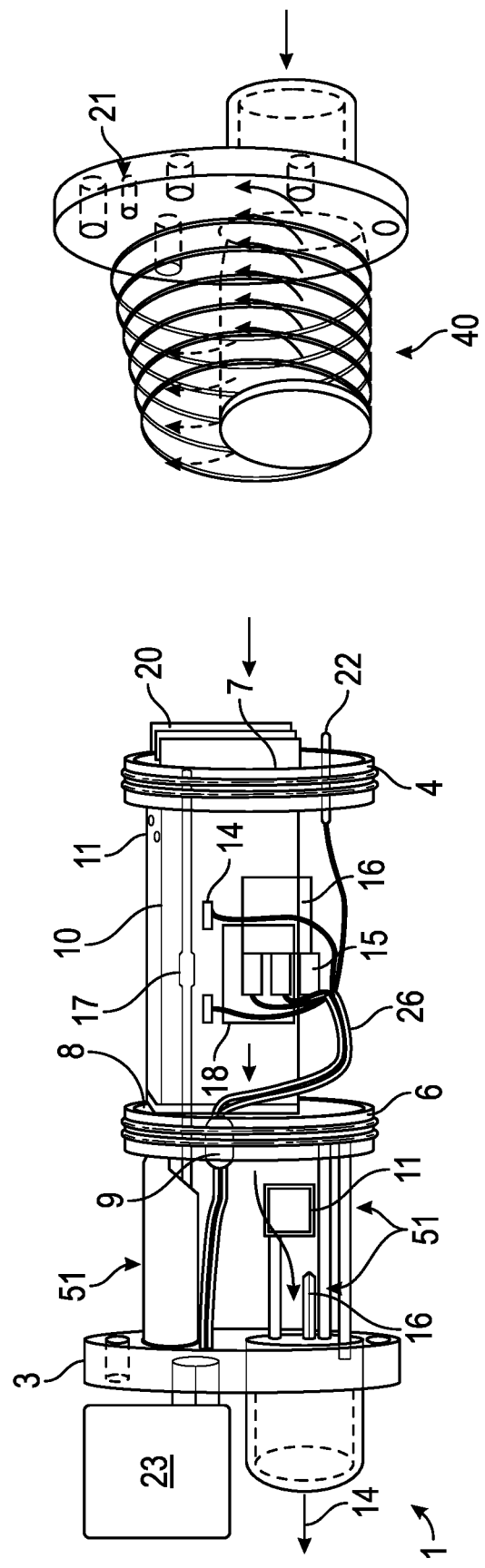
FIG. 1

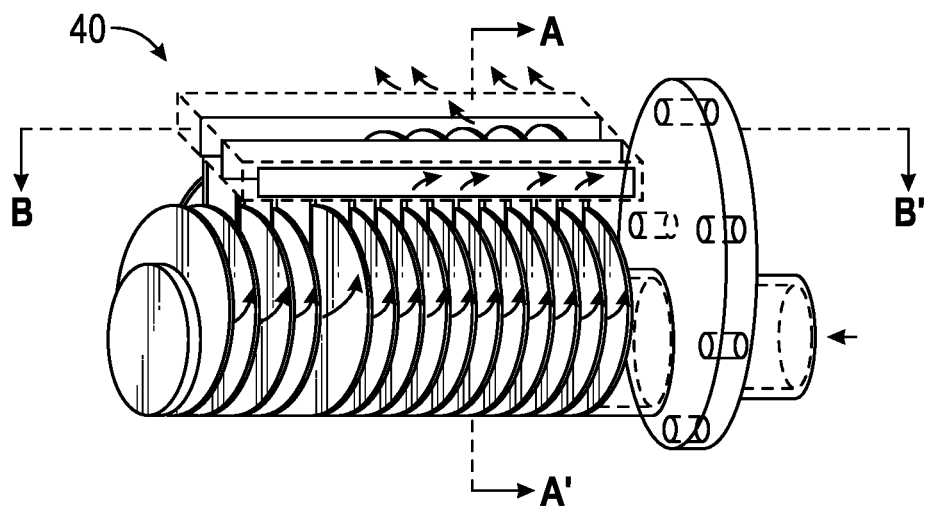
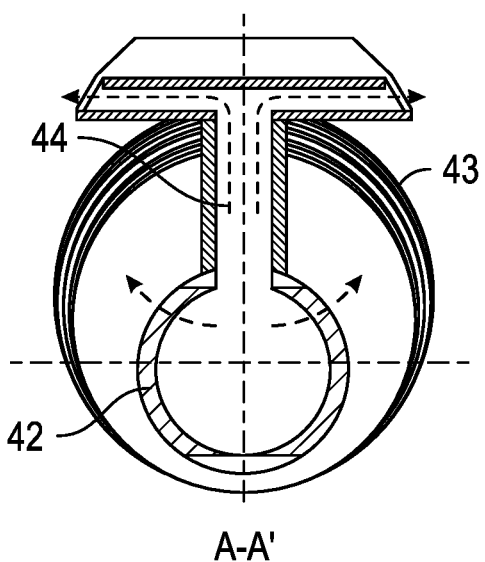
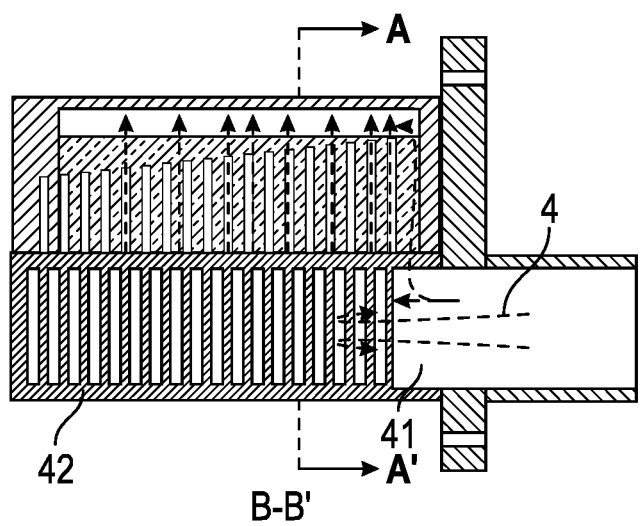
FIG. 2

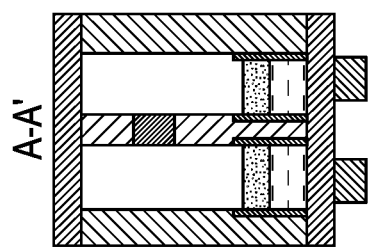
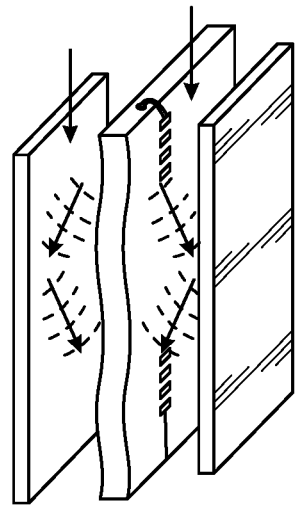
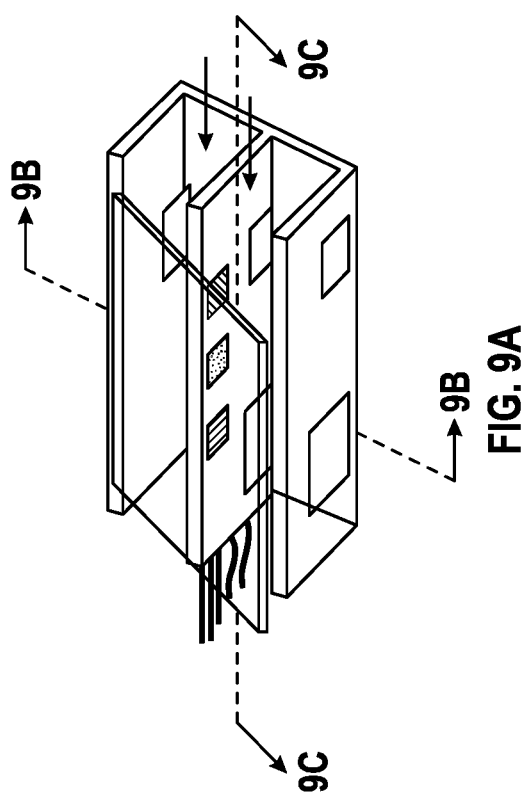
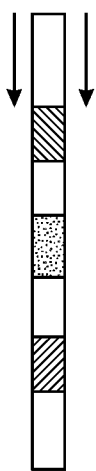

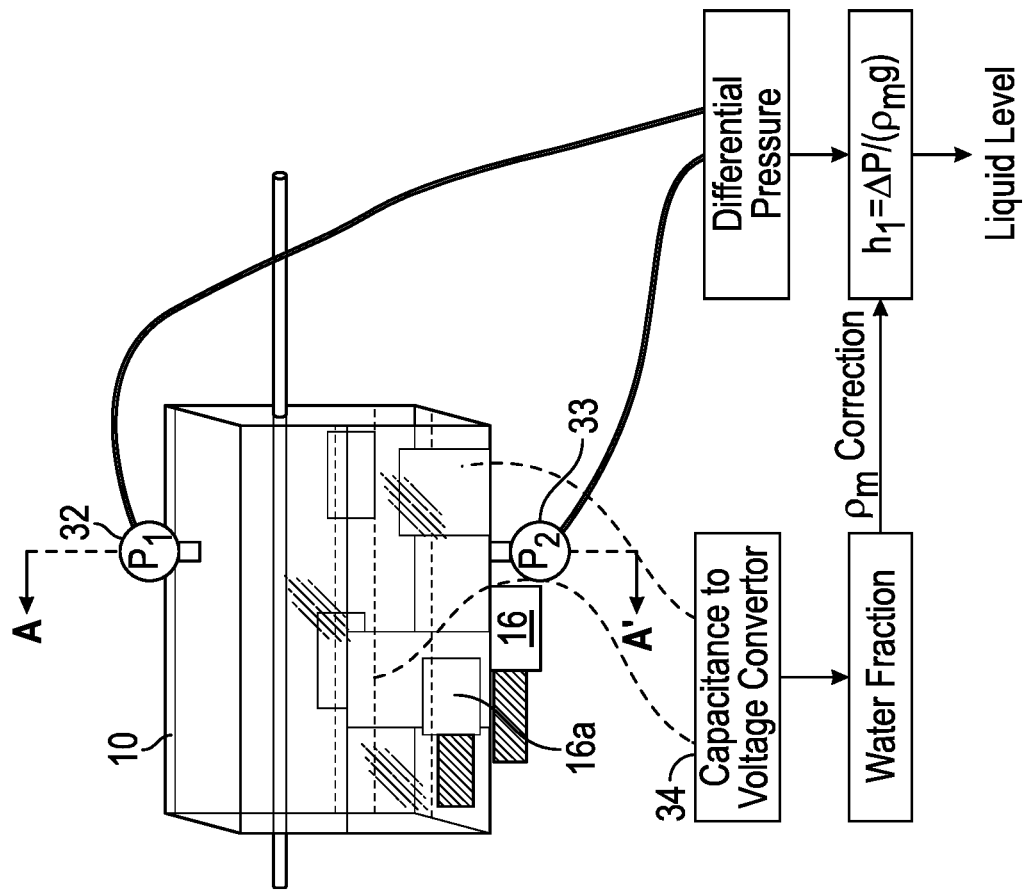
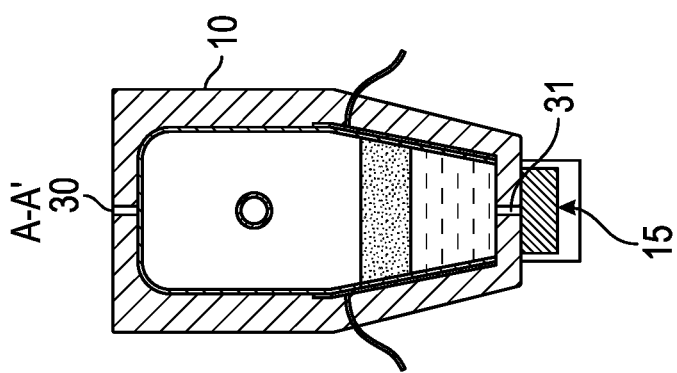
FIG. 10

FLOW MEASUREMENT INSERT

CROSS-REFERENCE TO RELATED APPLICATIONS

Priority is claimed from GB Application No. 1520706.1 filed on Nov. 24, 2015 and incorporated herein by reference in its entirety.

BACKGROUND

This disclosure is related to measuring a multiphase flow of oil, gas and water in a surface production pipe, which may be connected to an oil/gas producing well. The intended use of the disclosed apparatus is as a low-cost and nuclear-free multiphase flowmeter for low producing oil wells, which typically have moderate liquid flow rate of less than 1000 barrels/day and gas volume fraction (GVF) of not much greater than 90%. A flowmeter for such applications should be able to measure the oil flow rate, gas flow rate as well as water flow rate, while meeting requirements on pressure drop and cost limits. Such a flowmeter should also have a sufficiently wide flow rate measurement range (also referred to as the turn-down ratio), in order to cope with large variations in production flow rate during the life of the well.

There are mainly two types of approaches to multiphase flow measurement. The first is to measure the flow as a homogenized mixture of different phases, in which global parameters such as mixture density and velocity are measured to determine the flow rates. For the gas phase that always travels faster than the liquids, some kind of slip correlation is used to estimate its velocity. A typical example of this type is the Vx flowmeter produced by Schlumberger, which combines nuclear based phase fraction measurements with Venturi based differential pressure measurement to determine the flow rates of the three phases, oil, gas and water. The second approach is to separate the phases, according to their densities, so that separate velocity and holdup measurements can be applied to each of the individual phases.

The present application provides a flowmeter based on a single straight section of a pipe with only two end flanges, using inserted structures that may be made with relatively low-cost materials, and by relatively low-cost manufacture methods, to create flow channel structures.

SUMMARY

This disclosure describes methods and apparatus for measuring multiphase flow of fluids produced from an oil well. The basic apparatus is based on a near horizontal pipe setup that consists of a straight pipe section in combination with appropriate inserts mounted on one or both end flanges, with the said inserts creating a desired internal flow channel with appropriate shapes of cross-section variations that facilitates the separation of gas, oil, water into stratified three-phase gas/oil/water flows. The insertions also facilitate installation of various flow velocity and holdup measurement sensors around the walls of the internal flow channel or inside the flow path of one or more phases. The holdups and velocities of the three separated phases flowing in the internal channel are measured by sensors based on various principles such as ultrasonic, electromagnetic, thermal, etc. These measurements are combined with the flow channel geometry to derive the flow rates of the different phases. The end flanges also facilitates electrical feed-throughs that provide power and signal communication channel links between external electronic units and the sensors as well as the associated electronics and/or processing units inside the pipe. Embodiments of the present disclosure provide a low cost flowmeter that is simple to manufacture and install, and, with the fluid contained inside a single standard straight pipe-section between two flanges, satisfies operational safety requirements.

The above concepts for the measurement system are met by means of the multiphase flow measurement insert according to claim 1. In particular, the insert is intended to be introduced into a flow vessel, preferably the flow vessel being a standard pipe for use in the petroleum or normal fluid carrying industries. The particular advantage of this disclosure being that the pipe can be readily introduced or bolted onto the normal fluid carrying pipes of the petroleum network, and therefore this measurement system is readily adapted to be included in a variety of locations. The particular design of the insert is one provided with a plurality of isolation discs, wherein these discs are provided one upstream and one downstream when the insert is included into a pipe fluid carrying vessel. The isolation discs are appropriately structured such that they will form a fluid tight seal with the flow vessel, and this can be achieved in any number of known ways. Evidently, the size of the isolation discs is not fixed and can be chosen dependent upon the flow pipe into which the insert will be placed.

Within the first of the isolation discs, that which is intended to be positioned upstream and receive the inflow of fluid through the fluid transport network, is provided a first orifice passing therethrough. The second downstream isolation disc is also provided with an orifice, wherein the orifice in the first upstream isolation disc is generally provided higher than the orifice in the second downstream disc. The orifices in each of the isolation discs are smaller than the isolation discs themselves. A measurement vessel or tube is provided which joins the two isolation discs together, wherein this vessel is provided between the two orifices on the upstream and downstream isolation discs. The measurement vessel, or pipe, forms a fluid-tight seal around the two orifices, and allows for a fluid connection from the upstream side of the first isolation disc through the vessel to the downstream side of the second isolation disc. The measurement vessel forms a fluid channel which is generally downwardly sloped, as a result of the two orifices being at different heights and the measurement vessel tracking between these two orifices. The measurement vessel will, therefore, have a generally downward slope when it is put into the tube for making measurements.

By providing a downwardly sloped tube, the different phases in a multiphase fluid are encouraged to separate, and thus stratified flow may be achieved. The insert is intended to encourage the gas flow and liquid flows of a multiphase fluid to separate, such that the liquid will flow on the lower portion of the measurement vessel or flow channel and therefore stratified flow will be formed and improved measurement can be made on the fluid flow.

In order to further encourage fluid flow in a stratified manner, the insert comprises a flow resistance and straightening device at the orifice on the first upstream isolation disc. This straightening device will encourage the fluid passing through the orifice to slow down, and thus the two phases will separate such that stratified flow is also encouraged in the measurement vessel. The resistance and straightening device is made up of one or more parallel plates, which extend preferably vertically in front of the upstream side of the orifice in the upstream isolation disc. Selecting the gap between these plates and the length of the flat plate-like parts will allow for the speed of the fluid passing through this resistance device to be tailored, such that different flow regimes can be accommodated and stratified flow in the measurement vessel achieved.

It is further possible to provide secondary plates in the resistance device, wherein these plates are preferably horizontal or at approximately 90° plus or minus 5° to the first plates. These secondary plates not only assist in maintaining the parallel nature of the first plates, they also allow for further straightening of the fluid passing through the resistance device in order to promote stratified flow further downstream.

Given that the slope of the measurement vessel may be tailored, and the resistance device can also be appropriately structured, a position in the measurement vessel can be calculated in which stratified flow of a particular nature should, and typically will, be achieved. As a result of this structure it is then possible to provide a series of sensors which appropriately align with the portion of the measurement vessel in which stratified flow is to be achieved, thus improving the accuracy of the flow measurements being made.

The sensors can be positioned in a moveable manner such that if the flow characteristics of the fluid change, it is a simple matter to modify the insert and change the position of the sensors in order to ensure they align correctly with the area of stratified flow. This a significant advantage in that it allows for the insert to be readily tailored to any changes in the fluid flow system.

It is possible to position the sensors on the outside of the measurement vessel, which has the further advantage of these sensors not being affected by the fluid flow through the measurement vessel, and also allows for easier repositioning of the sensors around the measurement vessel. In particular, the sensors should have a small footprint such that they do not extend outside of the shape which would be defined by connecting the two isolation discs together. That is, the sensors do not increase the cross-sectional area of the insert, thus allowing the insert to be positioned within a flow pipe without damaging the sensors.

Numerous possible sensors are provided around the measurement vessel, wherein these can be relate to ultrasonic gas flow velocity sensors. These are preferably positioned at the upper part of the measurement vessel, wherein these can be positioned along the length of the measurement vessel at a point where gas flow is known to be in the upper portion therefore improving the measurement accuracy thereof. Likewise, ultrasonic liquid fraction and velocity sensors may be provided along the length of the measurement vessel where stratified flow is guaranteed, and these would then be positioned on the lower portion of the measurement vessel. Additional temperature sensors and pressure sensors can be provided, in order to make appropriate readings within the measurement vessel.

Given that stratified flow can be appropriately achieved in the measurement vessel, it is also advantageous to provide a water height sensor within the flow portion of the measurement vessel. One particular technique of providing the same is by means of a capacitive sensor, wherein an insulated conductor in the form a dipstick or dip ring is positioned within the fluid flow. The conductor is insulated from the liquid flowing through the measurement vessel and will form a capacitive reading with the water as a second electrode which is passing through the vessel in the stratified flow portion.

It is of significant advantage to have regions of known stratified flow as this allows not only for accurate measurements of liquid flow and gas flow, but also the accurate determination of the water height as this will separate out from the oil layer in such stratified flow regimes.

In order to allow connection through to the sensors between the two isolation discs, one or other of the isolation discs, or indeed both, may be provided with pressure-tight and/or fluid tight feedthroughs.

In order to encourage the stratified flow, the relative heights of the orifices through the two isolation plates may be modified and the inclination of the measurement vessel appropriately tailored. Depending upon the expected flow characteristics of the multiphase fluid, the angle of inclination of the measurement vessel could be between 0 and 45°, preferably between 0 and 30°. It is also more preferable to have the inclination between a range of 0 and 20°, preferably 0 to 15°, more preferably between 0 and 10° and further preferably between 0 and 5°. Obviously, the more horizontal the measurement vessel, the smaller the diameter of the pipe in which the insert is to be placed. This has the advantage of improving the space requirements for the combined system incorporating an insert.

A flow measurement system incorporating a housing in which the insert discussed above is to be placed, can be used to integrate with the flow pipes in a fluid flow processing system. In particular, the housing of the flow measurement system is structured and will make a fluid-tight seal with the two isolation discs, by appropriate choice of the size and shape of isolation discs. The housing comprises an inlet or inflow orifice which will fluidly couple to the upstream flow pipe in the liquid handling network. The lower portion of the inflow pipe advantageously aligns with the lower portion of the housing, such that the flow of liquid into the housing is not overly disturbed, which encourages the separation of gas and liquid phases. By ensuring that the housing is of a particular size such that a gap will be formed between the first sidewall or flange in which the inflow pipe passes and the upstream isolation disc, an accumulation volume can be defined. This accumulation volume allows for the inflowing multiphase fluid to settle and the two phases to appropriately separate prior to passing through the orifice in the upstream isolation disc into the measurement vessel. When the insert is placed within the housing, the orifice in the upstream isolation disc will be above the lowest side of the inflow pipe bore, such that the accumulation volume will allow for fluid to collect and any changes to the flow rate can be appropriately dampened. This further encourages stratification of the phases and improved flow through the measurement vessel.

In order to encourage the separation of the two phases entering the housing, the housing can also comprise a phase distributor provided adjacent the inflow from the fluid handling network. The phase distributor is structured such that the multiphase fluid entering the housing and accumulation volume will be slowed and encouraged to separate, such that the liquid is directed sideways and to the lower portion of the accumulation volume, whereas gas is encouraged to rise and be positioned in the upper portion of the accumulation volume.

The accumulation volume further preferably comprises a phase distributor at the interior side by the inflow orifice. The phase distributor operates in such a manner that the flow entering from the inflow pipe will be appropriately directed such that the different phases can separate and the liquid flow remains near the bottom of the accumulation volume, wherein the gas flow moves upward toward the higher portion of the accumulation volume. This also assists in the generation of stratified flow.

The structure of the phase distributor is one in which a central pipe is provided which fluidly connects to the orifice through which the multiphase fluid passes. The pipe is provided with a series of side slots, at least one thereof. The side slots are positioned to encourage the liquid part of the multiphase fluid to pass through the sides and enter the lower portion of the accumulation volume. In order to direct the liquid flow away from the central pipe, a series of fins are provided wherein the fins generally reduce in size as the pressure of the fluid in the internal pipe drops. This reduction in fin size assists in distributing the fluid within the accumulator.

The end of the pipe of the phase distributor is preferably blocked, as this ensures that the fluid does not immediately pass through the pipe and ends at the accumulation volume without being appropriately directed, this assists with the phase separation. One or more slots are provided in the upper side of the tube in order to allow the gas phase to appropriately separate out and enter the upper part of the accumulator. A preferred design for the upper slot is that of a T, wherein the side parts of the T-structure encourage the flow of gas to the outer and upper portions of the accumulation volume, thus improving the generation of stratified flow.

Within the measurement system, a second sidewall or flange is positioned at the downstream side which will then be further positioned further downstream from the downstream isolation disc. The sidewall or flange comprises an outflow orifice which will connect with the outflow pipe of the fluid handling network, wherein ideally the lower edge of this outflow orifice aligns with the lower edge of the inflow orifice in the first flange or sidewall. A downstream accumulation volume is obtained between the downstream isolation disc and the outflow orifice in order to allow for the fluid which has passed through the measurement vessel to appropriately gather, and thus avoid backflow of fluid into the measurement vessel. This is achieved by having the lowest point of the orifice in the lower isolation disc being above the lowest point of the outflow orifice of the housing, thus meaning that fluid flow will be encouraged out of the measurement system into the fluid handling network.

The downstream accumulation volume may comprise a series of supports which attach the insert mechanically to the downstream sidewall or flange and define the positioning of the insert with respect to the outflow orifice and downstream sidewall or flange. Furthermore, a series of feedthrough connectors may be provided within this downstream accumulation volume in order to feed through electrical, mechanical, optical connections and/or the like to the sensor arrangement. The size of the downstream accumulation volume may be changed by increasing or decreasing the size of the supports are required, and therefore the system can be appropriately tailored to different fluid flow volumes and velocities.

In order to ensure that the two accumulation volumes can handle the incoming multiphase fluid, the two volumes have a cross-sectional area which is at least twice the cross-sectional area of the housing inlet orifice and fluid handling pipework. Additionally, the length of each of the two accumulation volumes is at least twice the diameter, or maximum dimension, of the inflow orifice and inflow pipe. The measurement vessel preferably has a larger cross-sectional area than that of the inflow pipe, but a smaller cross-sectional area than the upstream and downstream accumulators. This helps to ensure that the flow of fluid through the measurement vessel is in a stratified form, but of course also allows for the vessel to be housed within the surrounding pipework or container. Further, the measurement vessel has a length which is at least twice the diameter of the housing inlet orifice, as this will ensure that the measurement vessel is long enough to have portions of guaranteed stratified flow. The length of the measurement vessel can be tailored depending upon the flow of multiphase fluid, and therefore the system is open to be tailored to different environments.

It is finally preferred for the vessel or housing holding the insert to be made of commercial piping, perhaps using standard commercial sizes between 3 inches and 32 inches, but preferably between 4 inches and 12 inches in diameter and between 1 and 3 metres long. Furthermore, the sidewalls are provided by normal flanges which can therefore be fluidly connected to the inflow and outflow pipes in the normal manner. The space between the upstream isolation disc (4) and the downstream isolation disc (6) can be filled will an inert liquid and pressure equalization between this external space and the internal portion or the fluid bearing side of the insert can be achieved by using pressure transparent devices such as a bellow between the internal and the external spaces. As a result, it is possible for the insert to be formed by relatively cheap and chemically inert materials, such as plastics, and indeed it is also possible to 3D print the insert which allows for further designs and tailoring to the system.

DESCRIPTION OF THE FIGURES

The present disclosure is described in conjunction with the appended figures. It is emphasized that, in accordance with the standard practice in the industry, various features are not drawn to scale. In fact, the dimensions of the various features may be arbitrarily increased or reduced for clarity of discussion.

FIG. 1 illustrates a straight pipe with inserted internal structure to implement a stratified flow generator and measurement arrangement suitable for measuring stratified gas/liquid or gas/oil/water flows, with ultrasonic or thermal based gas flow measurement system, a primarily ultrasonic Doppler based liquid flow measurement system, a capacitance/conductance based water holdup sensors, as well as additional P, T, and salinity measurement sensors, in accordance with some embodiments of the present invention.

FIG. 2 illustrates an upstream flange plate with inlet flow pipe on one side and an example fluid phase distributor on the other side—with different profile views showing the structure, in accordance with some embodiments of the present invention.

FIG. 6(a) illustrates installation options of an ultrasonic transit time based velocity measurement system;

FIG. 6(b) illustrates a non-invasive Lamb wave (flexural mode) based system with depicted V-shaped beam path and anti-reflection barrier;

FIG. 6(c) illustrates an invasively installed direct transmitting/receiving ultrasonic transit time measurement system.

FIG. 7(a) illustrates a thermal principle based gas velocity sensor that performs differential heat transfer measurement by measuring temperature difference between two points located symmetrically upstream and downstream of a heater, which is then inverted to determine gas flow velocity.

FIG. 8(a) illustrates one insulated electrode sensor (with connection wire) for separate water layer measurement with water as second electrode whose connection to measuring circuit, wire ii, is via a conducting electrode exposed to water with equivalent sensor model drawn below;

FIG. 6(b) illustrates capacitance sensor with two parallel-plate insulated electrodes for mixture permittivity measurement—applicable to oil-continuous emulsions, with equivalent model showing two insulation capacitances in series with the sensor capacitance;

FIG. 6(c) illustrates use two contact electrode plates to form a conductance cell, one electrode on each side of the flow channel, to form a parallel-electrode conductance sensor for mixture conductivity measurement—applicable to water-continuous emulsions;

in (b) or (c) the use of a mixing law may be used to derive WLR from the measured mixture permittivity or conductivity FIGS. 9(a)-(d) illustrates variations of the metering section cross-section configuration—example of using a central sensor bearing plate—in accordance with some embodiments of the present invention, where:

FIG. 9(a) illustrates the overall structure;

FIG. 9(b) illustrates cross-section showing the electrical impedance electrodes for water level/WLR measurement and part of a thermal sensor for gas velocity measurement embedded in the central wall;

FIG. 9(c) illustrates a cross-section of the thermal gas velocity sensor on the central plate; and FIG. 9(d) illustrates generating a Lamb wave (a flexural mode) in the central plate to produce a transit time ultrasonic gas flowmeter with embedded inter-digital transducer arrays FIG. 10 illustrates combining a measured water level or WLR with a vertical differential pressure measurement to derive a liquid level/holdup—an alternative/backup to ultrasonic methods, in accordance with some embodiments of the present invention.

Figure 3:
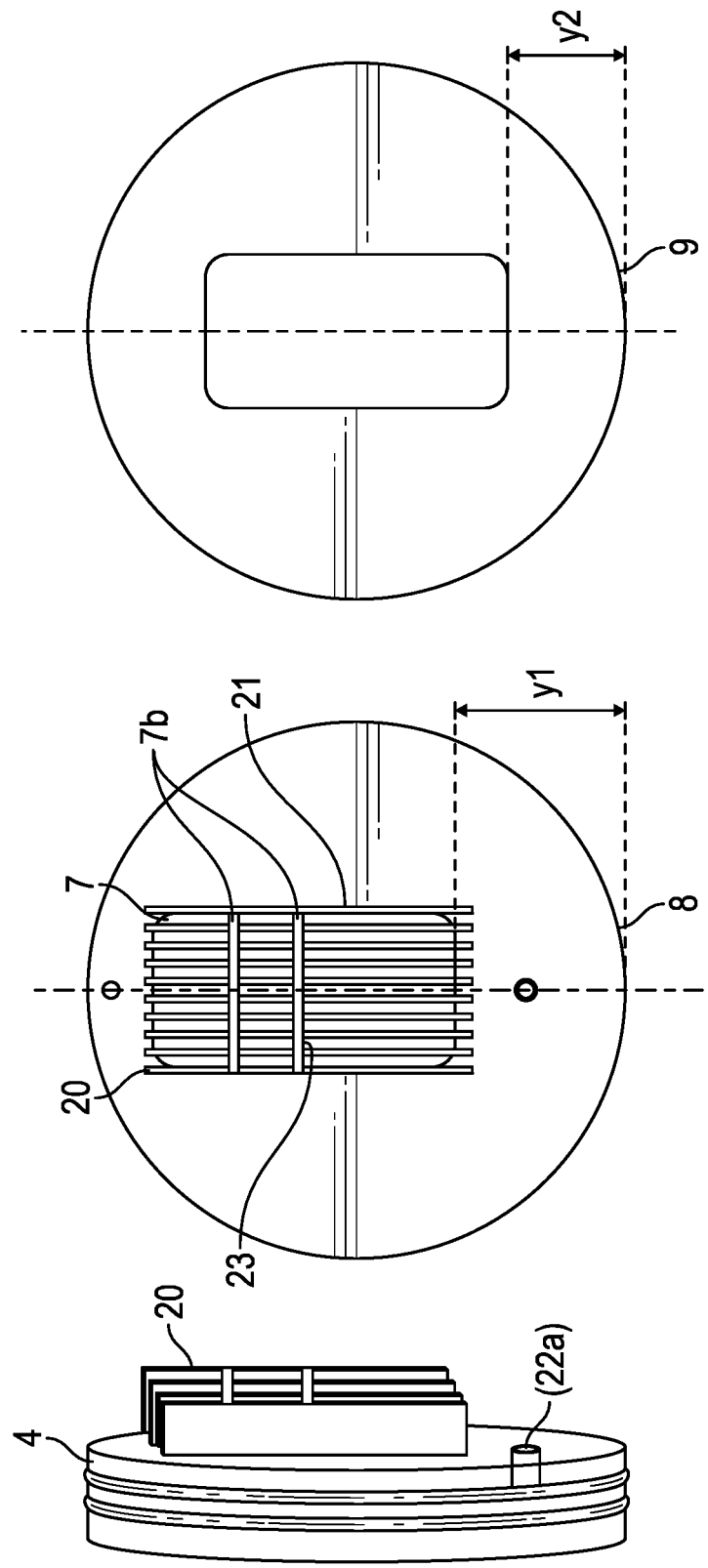
FIG. 3 illustrates two isolation discs at either end of a metering section, showing one example design of the flow resistive device on the first disc and the outlet location on the second disc which is shifted down by y1-y2, with respect to the position of the inlet, due to the deviation requirement of the metering section, in accordance with some embodiments of the present invention.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DESCRIPTION

The ensuing description provides preferred exemplary embodiment(s) only, and is not intended to limit the scope, applicability or configuration of the invention. Rather, the ensuing description of the preferred exemplary embodiment(s) will provide those skilled in the art with an enabling description for implementing a preferred exemplary embodiment of the invention. It being understood that various changes may be made in the function and arrangement of elements without departing from the scope of the invention as set forth in the appended claims.

Specific details are given in the following description to provide a thorough understanding of the embodiments. However, it will be understood by one of ordinary skill in the art that the embodiments maybe practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" includes, but is not limited to portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents.

Information, arguments, parameters, data, etc. may be passed, forwarded, or transmitted via any suitable means including memory sharing, message passing, token passing, network transmission, etc.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Embodiments of the present disclosure provide a multiphase flow system 30 created by inserting appropriate flow conditioning structures as well as various multiphase flow measurement sensors, all inside a straight standard pipe section, (which in oil industry is typically a steel pipe of a standard size) via at least one of the two flange plates 32, 35 at either end of the pipe, with the flange plates providing not only inlet 35 and outlet 36 for the multiphase flow, but also various electrical cable feed-throughs for connecting internal sensors with external electronic units. The flange plates 32, 25 may also provide accesses for pressure 17 and temperature 16 sensors installed outside the flowmeter. In such an arrangement, there is no need to drill holes on the straight pipe section 2, 3, 31 and most of the flow measurement sensors are sealed inside the shell provided by the pipe with the two end flange plates 32, 25.

Appropriate flow conditioning can convert a slug flow into a stratified flow, thus extending the stratified flow regime over the entire range of the flow rates required to cover by the flowmeter. Typically, generating a stratified flow regime involves enhancing the gravity separation effect, which can be achieved by slowing the flow velocity down, or using a downwardly inclined pipe or a combination of both methods. Therefore the insertions disclosed here form a flow channel structure that facilitates the creation of a stratified gas/liquid two-phase flow or a stratified gas/oil/water three-phase flow. The inserted structure 1 utilizes combinations of gravity separation enhancing components such as accumulation volumes, flow resistance devices 20 and inclined downhill flow channels 10 to create stratification. It also carries various sensors inside the shell formed by the straight pipe, for measurements of the holdups and velocities of the stratified phases.

The inserted structure 1 can be designed to have its inside and outside pressure balanced by the flow pressure. Therefore the requirement for material strength is reduced. This means that that inserted structure 1 can be made with a low cost material, such as a plastic, ceramic or metal material, by a low cost manufacturer method, such as casting/molding or even 3-D printing.

An advantage of using a plastic material as the flow channel wall is that the acoustic impedance match between the wall and the fluid is much improved compared with the case of a metal or a ceramic channel. This improves ultrasonic measurements made through the channel wall.

Considering FIG. 1, the flowmeter consists of two instrumented flange plates 32 and 35 that seal the two ends of a flanged straight pipe section 2, 3, 31. The straight pipe section 2, 3, 31 is typically made of a commercial steel pipe with two standard connection flanges 32, 35 at each end, with a size ranging typically between 3-inch to 12-in and a length typically between 1 to 3 meters. Two instrumented flange plates 32 and 35 are made to seal the ends of this pipe section 2, 3 via standard flange connections with commercial gaskets (not shown). On the instrumented upstream flange plate 32, an inlet flow pipe 34 is attached from the outside and a phase distributor 40 is attached from inside. Preferably the entry pipe 34 is located below the center of the instrumented flange plate 32, such that the bottom of the pipe bore is more or less aligned to the bottom side of the straight pipe section 2, 3, 31. The multiphase flow carried by the inlet pipe 34 flows through the multiple narrow slots 42 on the distributor 40 into the accumulator volume 34 formed inside the straight pipe 2, 3, 31 between the upstream flange plate 32 and the isolation disc 4 that is inserted from the other end of the pipe section 2, 3, 31 via the downstream flange plate 35. The downstream flange plate 35 is also used to insert the metering section that carries various sensors, and the $2^{nd}$ isolation disc 6 that forms a downstream accumulation space 50 with the downstream flange plate 35, in order to prevent back-flow into the metering section due to the choking effect of the outlet pipe 37, whose axis is preferably at the same height as the axis of the inlet pipe 34.

The upstream accumulator volume 34 is formed inside the straight pipe 2, 3, 31 between the upstream flange plate 32 and the isolation disc 4. When this volume is sufficiently large, it acts as a mass storage reservoir, equivalent to a capacitor in an electrical circuit. The other important components of the accumulator 34 include an inlet fluid phase distributor 40 and an outflow resistance device 20. The structure of an embodiment for fluid phase distributor 40 is shown in FIG. 2, where a slot 44 is created in the axial direction along the topside of an internal flow pipe 41 to let most of the gas vent upwards via a T-shaped vertical channel and a number of narrow slots 42 are cut out on both side of the internal flow pipe section 41 that extends the inlet flow inside the accumulator. These slots 42, combined with appropriate guide plates 43, form a number of narrow flow exit channels in order to reduce turbulent mixing between the inlet flow and the fluids inside the accumulator volume 34. The gradually reduced size of the guide plates 43 along the axial direction is used to compensate the increased pressure drop due to increased flow rate along the axial direction.

The multiphase gas/oil/water flow is separated into three layers by gravity in the accumulator volume 34, which then flows into a metering section via a resistive device 20 installed on the isolation disc 4. The flow resistive device 20 is typically in the form of a grid or laminar structure that increases fluid/wall contact area and hence the friction. An example is shown in FIG. 3, where a number of preferably thin solid plates 21 are placed in parallel with respect to each other, forming many narrow vertical flow channels. A number of horizontal plates 23 can also be used to link up the vertical ones 21 in order to strengthen the structure. The combination of the accumulator 34 and the resistive device 20 forms a fluid version of an equivalent R-C filter in an electrical circuit. This flow filter converts the input slug flow into liquid level fluctuations in the accumulator 34.

The smoothened out-flow from the accumulator 34 flows into a downwardly inclined pipe section 10, in which a primarily stratified gas/oil/water flow is maintained and ready for measurements. The down-hill inclination angle typically ranges between 0° to 45° but preferably between 0.1° and 5°.

This section is referred to as the metering section. There are various sensors installed inside and/or outside the section walls to measure various flow parameters. In FIG. 3, the isolation disc 4 has 0-Ring or other suitable seals designed to stop liquid in the accumulator 34 leaking behind it to flood the sensors mounted around the exterior of the section walls. However, some small leaking/flooding into the space between the metering section 10 and the straight pipe 2, 3, 31 may be tolerated in other embodiments that use suitable rubber bladders filled with inert gases or other suitable fluids (e.g. silicone oil) to protect these sensors and their cable connections. FIG. 3 also shows a gas pressure balance hole near the top side of the isolation disc 4. This is to allow gas pressure equalization between inside and outside of the metering section 10, such that the burst pressure requirement of this section is much reduced and materials with lower cost can be used. Holes can also be drilled on the top side of the metering section for the same purpose. Note that in such a flowmeter the upper part of the accumulator 34 and that of the metering section is always occupied by gas due to the stratification design.

The design described in this disclosure facilitates the downward inclination of the measurement pipe section 10 by lifting upward the interface location of this pipe section to the first isolation plate 4, to an appropriate offset height of y1 above the bottom line of the straight pipe bore 2, 3, 31, and by keeping the other end of the measuring pipe section 10 at a smaller offset height, y2, above bottom line of pipe (1), i.e. y2<y1 (see FIG. 3). The deviation angle, θ, is determined by y1−y2 and the length of the metering pipe section (10).

Figure 4:
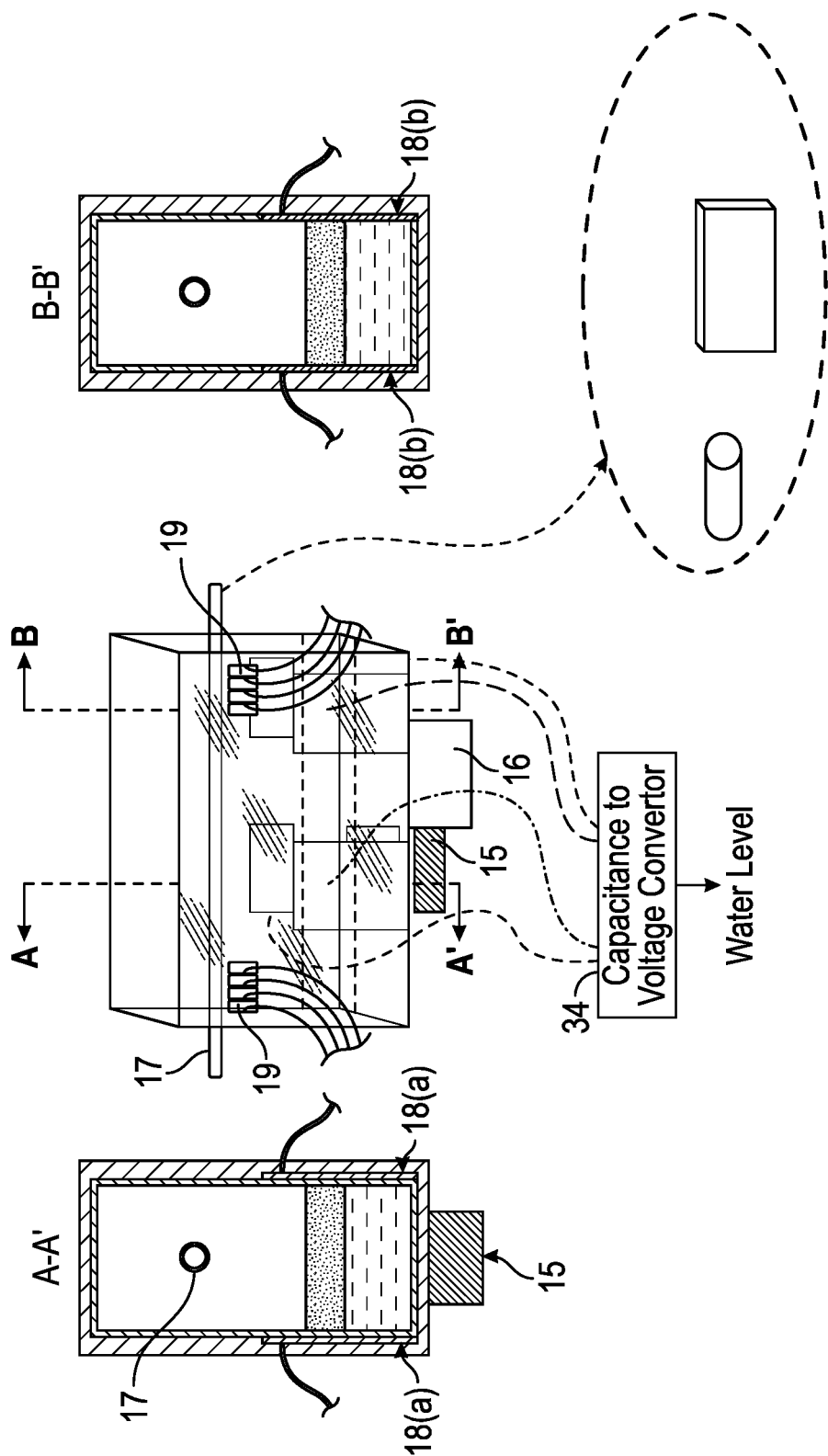
FIG. 4 illustrates structure and cross-sectional views of a flowmetering section with rectangular flow channel cross-section, including measurement options and example sensor installations for gas flow rate, liquid holdup and flow rate and water fraction measurement, including capacitance/conductance based water fraction sensors, gas velocity sensors and ultrasonic Doppler probes for liquid flow rate measurements, in accordance with some embodiments of the present invention.

The cross section of the metering channel 10 can have different shapes. In addition to a circular cross-section, elliptical, square, rectangular, isosceles trapezoid and other shapes can be used. FIG. 4 shows a metering section with a rectangular cross-section and FIG. 5 one with an isosceles trapezoid shape on the lower side of the flow channel. Such shape variations aim to produce sufficiently thick liquid levels in the metering section to allow required level measurement accuracy to be achieved for the entire flow rate range of the flowmeter.

Various parts of the inserted structure 1 such as the metering section the phase distributor 40, the resistive device 20 as well as isolation plates 4 and 6 may be made with a low cost and chemically inert material, such as CPVC for lower temperature applications of less than 82° C., or a high temperature plastic material such as PTFE, Nylon or PEEK for temperatures above that. The structure can be made with low-cost manufacturing methods such as casting, molding or even 3-D printing.

As shown in FIG. 1, the second isolation disc 6, the downstream flange plate 35, the supports 51 that links the disc 6 to the flange plate 35, various cables and additional sensors as well as the outlet flow pipe 37 form the last part of the flowmeter. The accumulation volume 50 formed between the disc 6 and flange plate 35 as well as the elevated metering section exit, defined by y2 (FIG. 3), helps to limit the back flows, which can be caused by the choking effect of the smaller sized outlet pipe 37, to within this volume (part number not shown), so that no fluids travels backwards into the measuring section that is further upstream. This ensures that the liquid level inside the metering section does not change significantly at different axial locations along the same pipe section 10. Preferably, the vertical offset y2 (shown in FIG. 3) is set to such a value that the gas/liquid interface level near the downstream end of the metering section is higher than the top of the exit pipe 37. This arrangement minimizes back-flow into the metering section.

For flows where the water and oil in the liquid phase is less cleanly separated, e.g. in the case of heavy oil producers where the density of oil is close to that of water, or where surface active oil components inhibit oil water separation, an additional water fraction sensor, e.g. a sensor based on electromagnetic principle such as microwave, can be placed at a location along the flow channel where the liquid flow is relatively most turbulent and the mixing between oil and water is strongest. This location is likely to be close to the exit from the metering section where the liquid flow flows down from the higher liquid level in the metering section to the lower gas/liquid level in the downstream volume, causing a certain degree of turbulent mixing. Measurement in such a location is likely to produce a more representative result.

Figure 5:
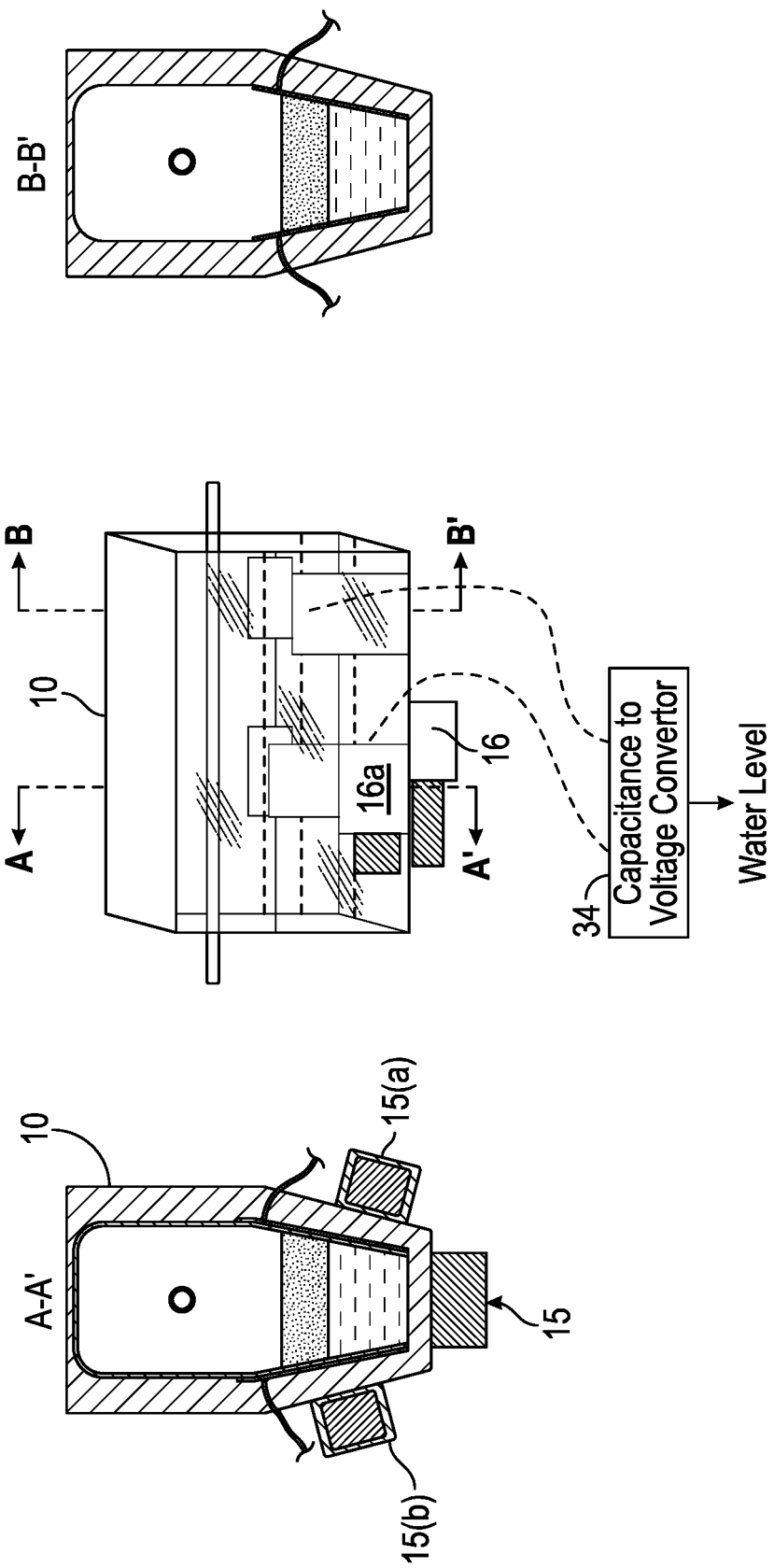
FIG. 5 illustrates structure and cross-sectional views of a flowmetering section with a partly isosceles trapezoid flow channel cross-section, including measurement options and example sensor installations for gas flow rate, liquid holdup and flow rate and water fraction measurement, including capacitance/conductance based water fraction sensors, gas velocity sensors and ultrasonic Doppler probes for liquid flow rate measurements, in accordance with some embodiments of the present invention.

FIGS. 1, 4 and 5 also show various options of measurement sensor installations for the metering section. These sensors, combined with the flow conditioning components formed by the insertion 1, provide a multiphase flow measurement system 30 specifically adapted to the metering of stratified gas/oil/water three-phase flows in oilfield pipes. The essential configuration may combine one or more of the following sensors/subsystems:

1. A gas flow velocity measurement unit 14 mounted above the central height of the pipe 10, to ensure that only gas phase is measured. The gas velocity sensor 14 can be based on various principles and deployed either intrusively in the gas phase or non-invasively outside the pipe wall 10. An example of an invasive deployment is shown in FIG. 1, which is a velocity sensor installed around the center of a deployment rod that extends the entire length of the metering section to avoid significant disturbance to the flow by its end. The sensor can be based on different principles such as heat transfer measurement or a turbine flowmeter. For a non-invasive example, two arrays of piezoelectric element, forming a transmitter-receiver pair, can be cemented on the outside of the channel wall to form a Lamb wave based ultrasonic transit time flowmeter, which is similar to a clamp-on flowmeter.
2. A gas pressure sensor 17 for line condition monitoring and gas flow rate pressure correction, which can be located in the metering section 11, on one of the flange plates 32, 35, since the absolute gas pressure change along the flowmeter is very small.
3. An ultrasonic liquid fraction and velocity measurement system 15, comprising at least one clamp-on ultrasonic Doppler transducer probe at the bottom side of the flow channel 10 and an ultrasound absorbing block in front of the probe. In the example of FIG. 5, more than one such probes and associated blocks are used to improve liquid flow measurement accuracy. These Doppler probes measure the liquid holdup and flow rate.
4. A water fraction sensor 18 based on capacitance and/or conductance principle with insulated capacitance electrodes 19 and exposed conductance electrodes.

Also either in the metering section or in other parts of the meter, a fluid temperature sensor 1 and an optional water salinity probe (22) can be included.

Outputs from these sensors/sub-systems are combined in a computation unit to derive the flow rate of oil, gas and water.

In ultrasonic gas velocity measurement systems 14, the gas flow velocity is measured by ultrasonic transit time based techniques on the upper half of the pipe 10. These techniques are widely used in commercial single phase gas flowmeters. In summary, the transit time method involves sending an ultrasonic pulse from transducer 1, receiving it at transducer 2 at a location downstream of the transmitter and measuring the first ultrasound transit time, t1, in the direction of the flow; then reversing the transmitter/receiver pair and obtaining a second transit time of the ultrasonic pulse, t2, in the direction against the flow. The combination of t1 and t2 as well as the path geometry between the transmitter and receiver allows the determination of the gas flow velocity as well as speed of sound.

As in a commercial ultrasonic gas flowmeter 14, the ultrasonic transducers can be insertion types that are directly in contact with gas, or clamp-on types that are mounted outside the pipe wall 10. For adaptation to this inserted metering section, FIG. 6a shows some example embodiments. In all cases, the transducers are installed in the upper part of the flow channel 11 so that ultrasound beam paths are in the gas phase only. FIG. 6b shows an embodiment that is a non-invasive measurement specially adapted to the insertion concept disclosed herein. A transducer array that consists of regularly spaced piezoelectric crystals along the flow direction can be installed (by cementing, clamp, etc.) onto the channel wall at an upstream location; whereas another identical array installed at a downstream location. In a typical measurement cycle, one of the arrays is used as a transmitter and the other as a receiver. To generate a Lamb wave of suitable mode, e.g. AO flexural mode, each transducer array may utilize a number of piezoelectric elements that have appropriate spaces between each other. Typically, a space equals to ¼, ½ or 1 wavelength of the flexural wave mode in the wall can be used and the elements can be excited by electrical voltage pulses with appropriate phase relationships to generate the desired flexural mode. This is known as inter-digital method for Lamb wave generation, which was used in the Non-destructive Testing (NDT) industry for detecting faults in wall materials, but was not used in transit-time based flow metering.

The flow channel wall, in which a suitable Lamb wave mode of a desired frequency is generated, acts as a waveguide. As the flexural wave mode is a leaky mode, the in-wall wave energy is continuously leaked into the flowing gas as it travels along the waveguide towards the receiving array, creating a wide beam of radiated energy across the gas flow. The radiation angle, θ, is defined by:

$$\sin(\theta) = c_{gas}/c_{flex} \quad (1)$$

where $c_{gas}$ is the speed of sound in gas and $c_{flex}$ is the flexural wave speed in the channel wall. When reaching the far side channel wall, this beam is reflected back towards the radiating waveguide wall, forming an inverted V-shaped path across the gas flow. When hitting the emitting wall, part of the through-gas wave energy converts back into the same flexural wave mode again in the waveguide, propagating towards the receiving array. The receiving array (TR2a) detects the arrival of this through-gas signal after the detection of the direct in-wall arrival. The time difference, Δt1, between the two arrivals provides the ultrasound transit time along the flow direction. Next in the second half of the cycle, the arrays are switched and the transit time against the flow direction, Δt1, is obtained. This allows the determination of both the flow velocity and the speed of sound in gas by using the transit time flow metering principle well published in the art.

Since the flexural wave propagating in the waveguide wall radiates to gases on both sides of the wall, there will be wave energy propagating from the (near-side) waveguide wall towards the space outside the flow channel where the air or gas filling the space is likely to be static or moving at a very different velocity to that inside the channel. For a normal clamp-on flowmeter, the space behind the transducer bearing wall is often open and no reflector will cause unwanted reflection back towards the receiver-bearing waveguide wall. However, in the insertion flowmeter described in this disclosure, the space behind the flow channel wall is limited and the outer pipe shell may produce reflected ultrasonic energy that interferes with the cross-flow-channel signal. In order to eliminate interferences from unwanted reflections, as a special feature of this disclosure, an acoustic scattering/absorbing barrier is placed behind the transducer bearing wall of the metering section flow channel. This barrier can be made with a combination of a rough scattering surface with an acoustic absorption material, such as a foam layer. The ultrasonic energy reaching this barrier will get absorbed and/or scattered and no unwanted reflection will be produced.

To summarize, the Lamb wave based transit-time gas velocity flow measurement arrangement applied to the insertion flowmeter, including 1) the use of embedded or clamp-on inter-digital transducer arrays for flexural mode generation/detection as part of the gas velocity measurement system and 2) the use of acoustic scattering/absorbing barrier behind the main wave guide—the transducer bearing flow channel wall, is considered as inventive.

Figure 6C:
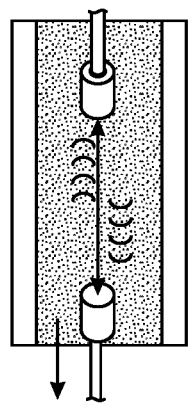
FIGS. 6(a)-(c) illustrates example arrangements of ultrasonic based gas velocity measurement system, in accordance with some embodiments of the present invention, where.
Figure 6B:
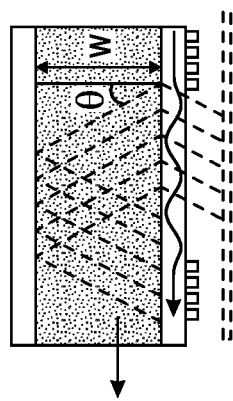
Figure 6A:
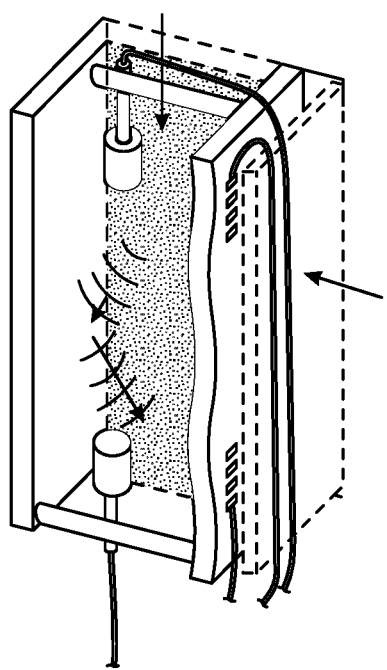

FIG. 6c shows another embodiment of an ultrasonic transit time based gas velocity measurement system 14. In this two ultrasonic gas-matched transducers are mounted face to face in the gas flow stream, separated by a known distance, L, with L much greater than the width of the channel. The transducers can be mounted by solid supporting beams near the two ends of the metering section, or through telescopic tubes directly attached to the flange plates 32, 35.

As alternatives to transit time based ultrasound gas velocity measurement, other type of velocity sensors can be mounted at the upper part of the measuring pipe section 10 to measure a velocity of the gas phase. These may include one or plural thermal probe(s), Pitot tube(s), spinner or turbine meter(s), or a vortex shedding based flowmeter. FIG. 7 shows two examples. In FIG. 7a, a gas velocity sensor based on heat transfer measurement is illustrated. The sensor consists of a cylindrical shaped heater with a certain heating power applied. Two equal sized temperature detecting rings are arranged in a symmetrical distribution about the heater, one upstream and one downstream. A thermocouple is embedded in each ring to measure the ring temperature. In a non-flow situation, the temperatures of the two rings are the same, due to the symmetrical configuration. When the gas velocity is greater than zero, the heat transfer processes become asymmetrical and the temperature of the downstream ring becomes higher than that of the upstream ring due to the direction of the gas flow enhanced convection. The temperature difference is a function of the gas velocity—the faster the gas flows the greater the temperature difference. Therefore the measured temperature difference can be inverted to give the gas velocity.

Figure 7B:
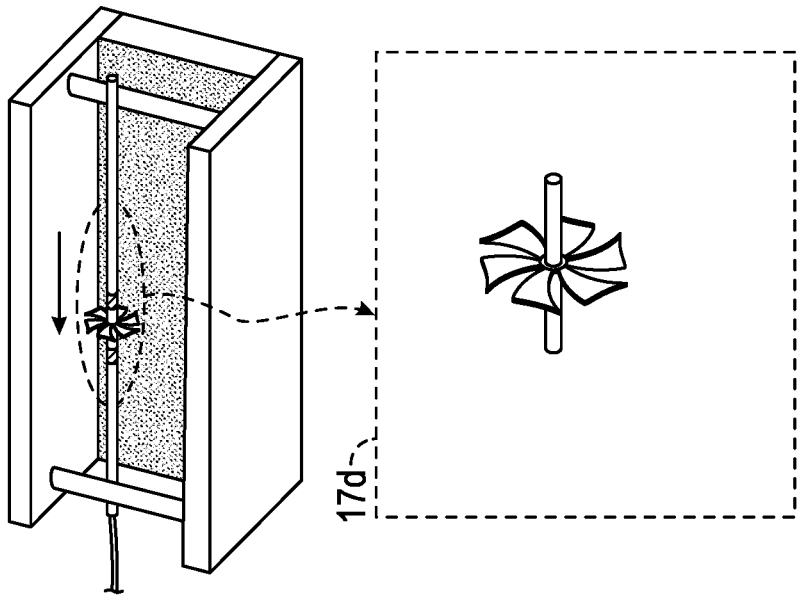
FIG. 7(b) illustrates a turbine-based gas velocity sensor
Figure 7A:
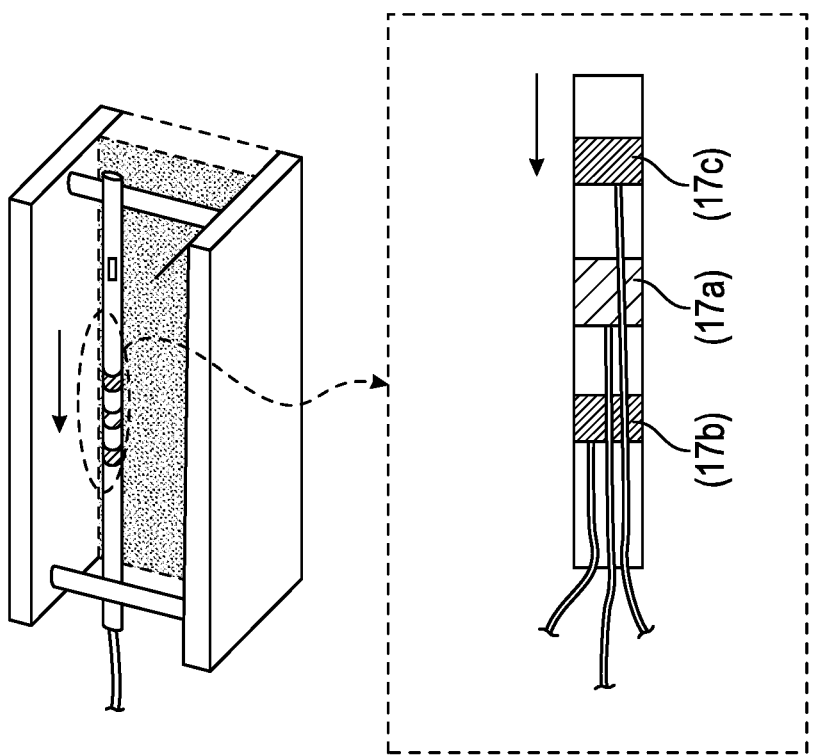
FIGS. 7(a) and (b) illustrate alternative methods of gas velocity measurement, in accordance with some embodiments of the present invention, where.

FIG. 7b shows a miniature turbine flowmeter for gas velocity measurement. It consists of turbine blades, a shaft and bearings at where the two ends of the shaft meet the support rods. The rotational speed of the turbine is measured by an appropriate detection circuit, which can be correlated to the velocity of gas.

The instantaneous liquid fraction signal from the range-gated ultrasonic Doppler system mounted around the lower periphery/circumference of the metering section is used to provide the instantaneous cross-sectional area of the liquid flow, $A_{liq}$. Knowing $A_{liq}$, the gas flow rate can be determined by:

$$Q_g = (A_p - A_{liq}) \cdot V_g \cdot P_s \cdot T_g / (P_g \cdot T_s) \qquad (2)$$

where $A_p$ is the pipe cross-section, $V_g$ the velocity of the gas phase, $T_s$ and $P_s$ the temperature and pressure at standard conditions, e.g. 293K and 1 bar, and $T_g$ and $P_g$ those at the line condition.

The range-gated ultrasonic Doppler system 15 with an array of sensors, typically clamp-on types, also provides velocity profiles along multiple paths over the cross-section of the liquid phase, see FIG. 5. If the oil and water separates into stratified layers, then the gas/liquid and the oil/water interface levels may be determined by the ultrasonic Doppler scan system. A more reliable and preferred method of measuring the water layer thickness is based on electrical capacitance principle.

Figure 8C:
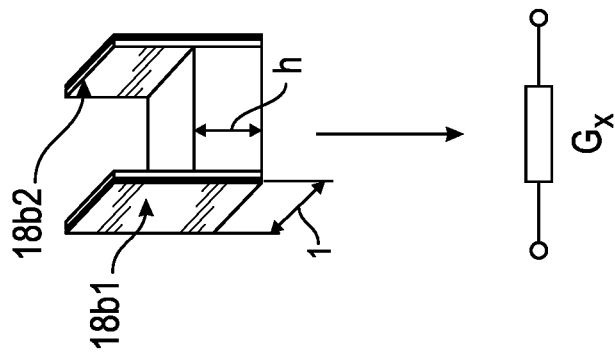
FIGS. 8(a)-(c) illustrate various electrical impedance based water holdup sensors, in accordance with some embodiments of the present invention, where.
Figure 8B:
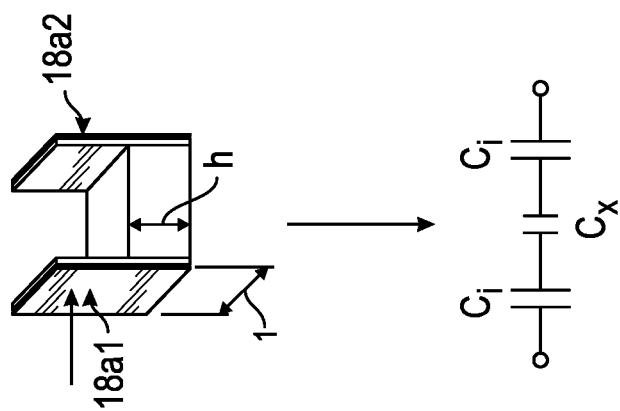
Figure 8A:
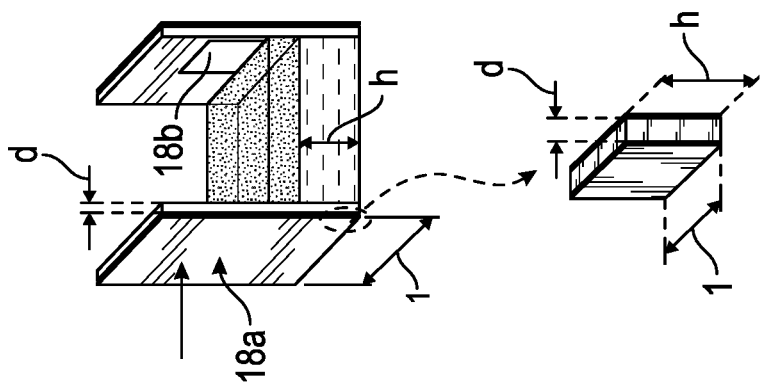

A number of embodiments of this are shown in FIG. 8. FIG. 8a shows an arrangement called one-electrode capacitive method. In this an insulated conductor 19 of a suitable shape and known geometry is immersed in water. This conductor 19 forms the first electrode of a capacitor, while the conductive water forms the second electrode, which is separated from the first conductor by the known insulation layer of the first conductor. In FIG. 8a, the conductor 18a is separated from water by an insulation layer of thickness, d. Electrical connection between water and a capacitance measuring circuit can be made through another conductor, as seen in FIG. 8a. Capacitance of the sensor 18 can then be measured by connecting the two cables, i and ii, to a capacitance to voltage converter circuit. The water contacting electrode 18b can utilize any metal piece that is exposed to water in the flow channel, as long as it makes a reliable electrical contact with the stratified water layer in the metering section. As long as the frequency of the electrode excitation waveform used by the measurement circuit is less than a few MHz, water can be treated as a perfect conductor in this application. Therefore the sensor 18 can be represented by an equivalent model as shown in the lower part of FIG. 8a, where the sensor capacitance is given by:

$$C = \frac{l \cdot \varepsilon}{d} h_w \qquad (3)$$

where l is the length of the electrode (a rectangular one in this example) in the flow direction, $\varepsilon$ the permittivity of the insulation material, d the thickness of the electrode insulation and $h_w$ the thickness of the water layer. Since, l, $\varepsilon$ and d are design parameters that set the gain of the sensor, the capacitance value is proportional to the water level $h_w$.

With the measured gas/liquid interface level (by ultrasound) and oil/water interface level (e.g. by capacitance), the flow rate of oil and that of water can be obtained by integrating the velocity profiles measured by the ultrasonic Doppler sensors 15 across the water and oil layers respectively.

If the liquid phase in the multiphase flow is a well-mixed oil-water emulsion, (for instance when the oil density approaches that of water in heavy oil wells) then the one-electrode method for stratified water layer measurement is no longer suitable. FIG. 8b shows a two-electrode conventional capacitance sensor arrangement, which can be used for water fraction or water-in-liquid ratio (WLR) determination in oil-continuous emulsions. The equivalent sensor model can be represented by the series capacitors as shown at the lower part of FIG. 8b, where $C_i$ represents the electrode insulation capacitance on either side of the flow channel. Since the insulation is much thinner than the channel width, w, the measured capacitance can be approximately expressed as:

$$C \approx C_x = \frac{l \cdot h \cdot}{w} \varepsilon_m \qquad (3)$$

where w is the width of the flow channel, h is the gas/liquid interface height, which can be measured independently by an ultrasonic sensor, and $\varepsilon_m$ is the mixture permittivity that one needs to measure. After determine the mixture permittivity from the measured capacitance, as a known practice for those familiar with the art, a mixing law can be used to derive the water-in-liquid ratio (WLR) from the measured mixture permittivity.

FIG. 8c shows a two-electrode conductance sensor arrangement that can be used for water in liquid fraction determination in water-continuous emulsions. The equivalent sensor model can be represented by a liquid conductance, as shown at the lower part of FIG. 8c. The measured mixture conductance can be approximately expressed as:

$$G_x = \frac{l \cdot h \cdot}{w} \sigma_m \qquad (4)$$

where w is the width of the flow channel, h is the gas/liquid interface height, which can be measured independently by an ultrasonic sensor, and $\sigma_m$ is the mixture conductivity of the emulsion. After determine the mixture conductivity, a mixing law can be used to derive the WLR from the measured mixture permittivity.

For the case of an emulsion, methods other than those described above can also be used to determine the WLR. For instance, this can be done through measuring the acoustic impedance of the liquid measured by an in-wall leaky wave mode, or through a liquid sampling and measurement device. With the WLR obtained, the Doppler velocity profiles over the entire liquid cross-section are integrated to derive the flow rate of the liquid phase, $Q_{liq}$. The oil flow rate is determined by:

$$Q_{oil} = (1 - WLR) \cdot Q_{liq} \qquad (5)$$

and water flow rate by $$Q_{water} = (WLR) \cdot Q_{liq} \qquad (6)$$

This concept can be implemented with different system designs. For example, in FIG. 9, where the flow channel of the metering section is divided into two halves by a central plate. This plate increases the contact area between the liquid phases and the channel walls, and hence the friction factor. For the same flow rate, this results in an increased liquid level and meanwhile a decreased flow velocity. The slower velocity helps to reduce the mixing at the oil/water interface, making the detection of the interface an easier task for either capacitance or ultrasonic sensors. FIG. 9a shows the overall structure and the concept of using this central plate also as a means for sensor deployment. For instance, capacitance, conductance electrodes can be embedded in the central plate wall to form measurement electrode pairs with those installed across the flow channel (FIG. 9b). The gas velocity measurement system based on the thermal principle (FIG. 9c) and that based on the Lamb wave transit time principle (FIG. 9d) can also be embedded in the central wall. In FIG. 9c, the heating element and the upstream/downstream temperature sensing elements may have their active surfaces exposed to gases on both side of the channel. In FIG. 9d, the Lamb wave (flexural mode) generated in the central plate will leak energy into gas flows in both half-channels and the measured flow velocity should be an average of the gas velocities on both sides. In this configuration, no ultrasonic anti-reflection barrier is needed.

As an alternative way of measuring liquid level, a differential pressure transducer or two absolute pressure sensors P1 and P2 can be installed on the metering section to measure the weight of a vertical liquid column as shown in FIG. 10. The measured differential pressure, $\Delta P=P2-P1$, is used in combination with the value of WLR measured by, for instance, an electrical impedance based sensor, to derive the liquid level. If the liquid is an oil/water emulsion, then we have $$\Delta P = \rho_m \cdot g \cdot h_l \quad (7)$$

where $\rho_m$ is the average density of the liquid phase and it is linked to the WLR via the following expression:

$$\rho_m = (WLR) \cdot \rho_w + (1-WLR) \cdot \rho_o \quad (8)$$

where $\rho_w$ is the density of water and $\rho_0$ that of oil, which can be determined by sampling and calibration. From $\Delta P$ and $\rho_m$ that is derived from (8), one obtains the liquid level:

$$h_l = \frac{\Delta P}{g \cdot \rho_m} \quad (9)$$

If oil and water are separated into two different layers, one may also combine the $\Delta P$ with a measured water level, $h_w$, (e.g. by capacitance method) to derive the gas/liquid interface level. The relationship between $\Delta P$ and $h_w$ is given by $$\Delta P = \rho_w g h_w + \rho_o g h_o, \quad (10)$$

where g is the gravitational constant and $h_0$ is the thickness of the oil layer, which can be determined by $$h_o = \frac{\Delta P - \rho_w g h_w}{\rho_o g}. \quad (11)$$

Once is $h_0$ derived, the liquid level can be obtained from the following relationship $$h_l = h_o + h_w. \quad (12)$$

Key aspects of this disclosure relate to combining appropriate flow conditioning devices that generate a stratified gas/liquid or gas/oil/water flow in a metering section 10 with various velocity and phase holdup measurement means tailored to determine the flow rates of the individual stratified phases such as gas and liquid and, inside the liquid phase, oil and water. In particular, i. Generation of a stratified flow by:
a) combining a first stage flow accumulation volume 34 with an inlet phase distributor 40 and a flow-out resistive device 20 to implement a flow filter that smoothens the slugging input flow from the upstream production pipeline 34,
b) further enhancing the phase stratification between gas, oil and water in a downwardly inclined flow channel 11 as a metering pipe section 10 that is installed downstream of the accumulator 40 and resistive-device 20 and
c) eliminating flow back into the inclined section by placing a downstream accumulation volume 50 between the end of this section and the outlet of the meter connecting to the downstream production pipeline 37, which ensures that the gas/liquid interface in the downstream accumulator 50 is generally lower than that anywhere in the inclined flow section 11
d) the flow channel structure 11 of the flowmeter described in a), including the upstream accumulator 34 with phase distributor 40 and resistive device 20, downwardly inclined metering section 11, downstream accumulator/conditioner 50, can be implemented by inserting structures 1, made with relatively low cost material and low cost manufacture method, into a straight pipe of sufficiently large diameter. The insertions 1 can be attached to the two flange plates 32, 35 at either end or both ends of the straight pipe 2, 3, 31.
More specifically
(1) With the cross-sectional area of the two accumulators 34, 50 significantly greater than that of the production pipe line 34
(2) For the first part of a typical upstream flow accumulator, using a flow direction diverter 40 and phase distributer 40 near the entrance to provide easier gas passage to the top part and distributed liquid passage to the lower part of the accumulator volume 34 to reduce cross-path and flow turbulence induced mixing between the phases,
(3) Using a flow resistance device 20 near the exit of the volume 34 to enhance the filtering and slug smoothing effect and reduce flow rate fluctuation in the inclined measurement pipe section 11 downstream;
(4) Create a downwardly flow in an inclined pipe 10, with a suitable, inclination angle, generally between 0 and 45 degrees, but preferably between 0.1 and 5 degrees, to enhance the stratified flow regime,
(5) The inclined pipe 10 provides the metering section, on which various sensors are installed for performing phase holdup, velocity and flow rate measurements.
(6) Different cross-section from circular may be used for the metering pipe section 10, including square, rectangular, oval, trapezoid and other shapes.
(7) Preferably, the bottom of the downstream accumulator 50 has an appropriate step down vertically from the bottom of the metering section pipe 10, such that the gas/liquid interface level near the downstream end 8 of the metering section 10 is generally higher than that in the downstream accumulator 50.
  a) the flow channel 11 structure of the flowmeter described in a), including the upstream accumulator 34 with phase distributor 40 and resistive device 20, downwardly inclined metering section 11, downstream accumulator/conditioner 50, can be implemented by inserting structures 1, made with relatively low cost material and low cost manufacture method, into a straight pipe of sufficiently large diameter. The insertions 1 can be attached to the two flange plates 32, 35 at either end or both ends of the straight pipe 2, 3, 31.

ii. Deploy various sensors/measurement systems on the metering section 10 to measure some, or all of the following multiphase flow-related parameters of the individual stratified phases separately:
gas phase flow velocity,
liquid phase flow velocity,
oil phase flow velocity,
water phase flow velocity,
liquid phase holdup or gas phase holdup,
water holdup, or water-in-liquid ratio (WLR),
water conductivity,
oil holdup Preferably with the velocity and holdup measurements performed on the same cross-section of the stratified gas/oil/water flow (about the same axial location).

iii. The preferred measurement techniques include:
a. An ultrasonic based gas velocity measurement system 14 with its beam path across the gas phase at the upper part of the flow channel: including transit-time based systems with transducers exposed directly to gas, or transit-time velocity measurement systems based on Lamb wave (flexural modes) in the flow channel wall of the metering section, which is generated using non-invasive clamp-on or embedded transducer or transducer arrays (driven by inter-digital methods); the ultrasonic transit time velocity measurement system also produce a speed of sound measurement as a by-product, which can be combined with gas temperature to produce a gas quality indicator; appropriate wave scatter/absorber is deployed in some cases to eliminate unwanted wave propagation path, e.g. those through static gas outside the flow channel.
b. A liquid phase measurement system 15 based on a number of (preferably non-invasive) ultrasonic transducers around the periphery of the metering pipe section, each performing a range-gated Doppler measurement, which allows the measurements of the gas/liquid interface level and velocity profiles across the liquid phase, and thus the derivation of liquid and gas holdups, the average velocity of the liquid phase and that of oil phase and water phase. When water and oil are well separated, the ultrasonic sensing systems also measures the oil/water interface level height and hence the water holdup.
c. An electrical impedance based water level or WLR sensor, including but not limited to the following:
1) A water level sensor 18 based on a one-electrode capacitance principle that utilizes one insulated conductor submerged in the stratified water layer as electrode 1 and water itself as electrode 2 and produces a capacitance sensor output as a function of water layer thickness
2) A WLR sensor with two capacitance electrodes, whose capacitance value is related to the effective permittivity of the liquid between them, which can be further interpreted to give the WLR of the liquid phase.
3) A WLR sensor with two conductance electrodes, whose conductance is related to the effective conductivity of the liquid between them, which can be further interpreted to give the WLR of the liquid phase.
4) A microwave based WLR sensor for both water-continuous and oil-continuous liquids.
d. Various alternative/backup sensors used in the stratified flow context:
1) Alternative gas velocity measurement sensors such as thermal based heat transfer sensors, turbine flowmeters, V-cone flowmeters, Pitot tubes, vortex shedding based measurement systems, etc.
2) Other interface level measurement methods such as vertically mounted differential pressure measurement, dipstick sensors based on Lamb wave, mechanical resonance sensors, etc.
3) Other liquid phase velocity sensors, such as cross-correlation based flow measurement systems, vortex shedding measurement systems, etc.
4) Other WLR measurement means such as an ultrasonic leaky wave sensor to measure the acoustic impedance of the liquid as a function of WLR, sampling of liquid mixture and performing off-line analysis, etc.

iv. As a preferred embodiment, the sensors/measurement systems listed in ii and iii are installed on the insertion structure 1 described in i-d), particularly around the inserted metering section, with connection cables linking the internal sensors with external electronics/processors via pressure tight electrical feed-throughs.

v. Combining various measured flow parameters to derive the flow rates of the gas, liquid, water and oil. For instance:
a) combining the gas cross-sectional area measured in iii-b and the gas velocity obtained in iii-a as well as measured gas temperature and pressure to produce the gas flow rate;
b) combining ultrasonic measured velocity profile across the water layer (iii-b) with the oil/water interface measured by capacitance (iii-c-1) and derive the water flow rate;
c) combining ultrasonic measured velocity profile across the entire liquid layer (iii-b) with the gas/liquid interface measured by ultrasound (iii-b) and derive the liquid flow rate;
d) calculating the oil flow rate from the difference of the liquid flow rate and the water flow rate vi. Fluid property measurements:
1. Use gas, liquid, water, oil sample lines in combination with an interface level measurement sensor to extract samples of separated phases from the upstream flow conditioner/accumulator 34, which is effectively a separator;
2. Use on-line fluid property sensors such as water conductivity probe and gas quality sensor to measure the properties of the separated phases.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The invention claimed is:

1. A multiphase flow measurement insert for insertion within a fluid flow vessel or pipe, comprising:
a first, upstream isolation disc configured to make a fluid tight seal with an interior surface of the fluid flow vessel or pipe when contained therein;
a second, downstream isolation disc configured to make a fluid tight seal with the interior surface of the fluid flow vessel or pipe when contained therein; wherein:
the first isolation disc includes a first orifice;
the second isolation disc includes a second orifice;
each orifice is smaller in cross-sectional area than the first and second isolation discs; and a lower edge of the first orifice is positioned vertically higher in the first isolation disc than a lower edge of the second orifice in the second isolation disc when the multiphase flow measurement insert is in its operational orientation; and a measurement vessel extending from the first orifice to the second orifice and configured to form a flow channel between the first and second orifices, wherein a lower edge of a first end of the flow channel aligns with the lower edge of the first orifice and a lower edge of the second end of the flow channel aligns with the lower edge of the second orifice such that the flow channel is downwardly sloping when the multiphase flow measurement insert is in its operational orientation.

2. The multiphase flow measurement insert of claim 1, wherein the measurement vessel comprises one or more sensors positioned at a location along the measurement vessel which, based on the geometry of the multiphase flow measurement insert and expected fluid flow through the measurement vessel, corresponds to a location in which stratified flow of the fluids passing through the measurement vessel will be obtained.

3. The multiphase flow measurement insert of claim 1, wherein either of the first and second isolation discs comprises wiring feedthrough holes.

4. The multiphase flow measurement insert of claim 1, wherein an angle of inclination as measured from a horizontal of the measurement vessel when in use is in a range of 0° to 45°.

5. The multiphase flow measurement insert of claim 1 constructed from a chemically inert material comprising one or more of CPVC, PTFE, Nylon, or PEEK.

6. A method for measuring multiphase flow in a fluid flow vessel or pipe, the method comprising:
inserting the multiphase flow measurement insert of claim 1 into the fluid flow vessel or the pipe; and
using the multiphase flow measurement insert to measure properties of a multiphase mixture flowing through the fluid flow vessel or the pipe.

7. The multiphase flow measurement insert of any claim 1, further comprising:
a water level sensor based on a capacitance measurement.

8. The multiphase flow measurement insert of claim 7, wherein the water level sensor comprises an insulated conductor in a dipstick or dip-ring configuration which is adapted to measure capacitance between the insulated conductor and any water in the measurement vessel to determine a height of the water, when present.

9. The multiphase flow measurement insert of claim 1, further comprising:
a flow resistance and straightening device disposed adjacent to the first orifice, wherein the flow resistance and straightening device comprises one or more primary flat plates mounted in parallel with respect to each other and extending either vertically or horizontally, the flat plate-like portion of the primary plates being aligned with the normal to the first orifice in order to reduce the flow of liquid into the measurement vessel and to straighten the flow thereof.

10. The multiphase flow measurement insert of claim 9, wherein the flow resistance and straightening device is coupled with the first isolation disc and is configured to cover the first orifice.

11. The multiphase flow measurement insert of claim 9, wherein one or more parallel secondary flat plates are provided in the flow resistance and straightening device rotated with respect to the primary flat plates, wherein preferably the angular offset between the primary and secondary flat plates is 90°+/−5°.

12. The multiphase flow measurement insert of any claim 1, wherein the measurement vessel comprises one or more sensors which are provided outside the measurement vessel and which are adapted to be moveably fixed to the outside of the measurement vessel.

13. The multiphase flow measurement insert of claim 12, wherein the one or more sensors are configured such that when attached to the outside of the measurement vessel the one or more sensors do not extend outside of the cross-sectional outline/silhouette formed between the first and second isolation discs.

14. The multiphase flow measurement insert of claim 12, wherein the one or more sensors comprise one or more of:
(a) ultrasonic gas flow velocity sensors mounted around or above the central vertical point of the measurement vessel;
(b) ultrasonic liquid fraction and velocity sensors mounted around or below the central vertical point of the measurement vessel-;
(c) temperature sensors; or
(d) pressure sensors located throughout the vertical height range of the measurement vessel.

15. A flow measurement system comprising:
the multiphase flow measurement insert of claim 1;
a housing comprising the fluid flow vessel or pipe, wherein the housing comprises a sidewall or flange comprising a housing inlet orifice for receiving an inlet pipe of a fluid transport system, wherein a lower edge of the housing inlet orifice aligns with a lower edge of the housing when in its operational orientation; and
an accumulation volume within the housing located between the sidewall or flange comprising the housing inlet orifice and the first isolation disc.

16. The flow measurement system of claim 15, wherein the cross-sectional area of each of the accumulation volume and the downstream accumulation volume taken as the normal to the housing inlet orifice is at least twice the cross sectional area of the housing inlet orifice, and the length of each of the accumulation volume and the downstream accumulation volume is at least twice the diameter of the housing inlet orifice, or longest side of the housing inlet orifice when this is not circular, and the cross sectional area of the measurement vessel is larger than the cross sectional area of the housing inlet orifice and smaller than the cross-sectional area of the accumulation volume and the downstream accumulation volume.

17. The flow measurement system of any claim 15, wherein:
the fluid flow vessel or pipe or housing is constructed from standard or commercial piping with a diameter of between 76.2 mm (3 inches) and 812.8 mm (32 inches), but preferably between 100 mm and 304.8 mm and a length of between 1 m and 3 m, the sidewalls of flanges are standard or commercial flanges for the piping.

18. The flow measurement system of claim 15, further comprising:
a phase distributer within the accumulation volume, the phase distributer positioned adjacent the housing inlet orifice such that fluid passing through the housing inlet orifice passes through the phase distributer, the phase distributer being adapted to distribute the liquid and gas phases of an incoming flow from the inlet pipe within the accumulation volume.

19. The flow measurement system of claim 18, wherein the phase distributer comprises:
- a pipe having a size and shape matching that of the housing inlet orifice;
- one or more first slots provided along the length of the pipe extending through a pipe wall to fluidly connect an inside of the pipe with an outside of the pipe, wherein the one or more first slots are located at sides of the pipe when the phase distributer is in its operational orientation;
- one or more fins located on the outside of the pipe and adjacent and between the one or more first slots, wherein the one or more fins have a larger cross-sectional area than a cross-sectional area of the pipe, and wherein the fins extend away from the outside of the pipe to direct a liquid phase flowing through the pipe outward and away from the pipe; and
- one or more second slots provided along the length of the pipe extending through the pipe wall to fluidly connect the inside of the pipe with the outside of the pipe;
- wherein the one or more second slots are located at a top of the pipe when the phase distributer is in its operational orientation, are configured to strip and divert the gas phase to an upper part of the accumulation volume, and are shaped as a "T"; and
- wherein a lower part of the accumulation volume is in fluid connection with the inside of the pipe and side arms of the "T" are adapted to direct the gas phase outward toward the sides of the accumulation volume.

20. A method for measuring a multiphase flow in a fluid flow vessel or pipe, the method comprising:
- flowing the multiphase flow through a measurement insert inside the fluid flow vessel or pipe;
- wherein the measurement insert is formed by a first isolation disc inserted in the fluid flow vessel or pipe and configured to make a fluid tight seal with an interior surface of the fluid flow vessel or pipe, and a second, downstream isolation disc inserted in the fluid flow vessel or pipe and configured to make a fluid tight seal with the interior surface of the fluid flow vessel or pipe when contained;
- wherein the first isolation disc includes a first orifice, the second isolation disc includes a second orifice; and each of the first and second orifices is smaller in cross-sectional area than the first and second isolation discs;
- wherein a lower edge of the first orifice is positioned vertically higher in the first isolation disc than a lower edge of the second orifice in the second isolation disc when the multiphase flow measurement insert is in its operational orientation;
- wherein the measurement vessel comprises a first end and a second end extending from the first orifice to the second orifice and configured to form a fluid tight seal with the first and second orifices to form a flow channel between the first and second orifices, wherein a lower edge of a first end of the flow channel aligns with the lower edge of the first orifice and a lower edge of the second end of the flow channel aligns with the lower edge of the second orifice such that the flow channel is downwardly sloping when the multiphase flow measurement insert is in its operational orientation; and
- using one or more sensors to measure properties of the multiphase flow flowing through the measurement insert.

* * * * *